(12) United States Patent
Crouse et al.

(10) Patent No.: US 11,941,331 B2
(45) Date of Patent: Mar. 26, 2024

(54) MULTI-PHASE FLOW VISUALIZATIONS BASED ON FLUID OCCUPATION TIME

(71) Applicant: Dassault Systemes Simulia Corp., Johnston, RI (US)

(72) Inventors: Bernd Crouse, Brisbane, CA (US); Rui Xu, San Francisco, LA (US)

(73) Assignee: Dassault Systemes Americas Corp., Waltham, MA (US)

( * ) Notice: Subject to any disclaimer, the term of this patent is extended or adjusted under 35 U.S.C. 154(b) by 0 days.

(21) Appl. No.: 17/897,310

(22) Filed: Aug. 29, 2022

(65) Prior Publication Data

US 2022/0414295 A1    Dec. 29, 2022

Related U.S. Application Data

(63) Continuation of application No. 15/880,867, filed on Jan. 26, 2018, now Pat. No. 11,461,512.

(Continued)

(51) Int. Cl.
*G06F 30/20*        (2020.01)
*E21B 43/16*        (2006.01)
(Continued)

(52) U.S. Cl.
CPC ............ *G06F 30/20* (2020.01); *E21B 43/16* (2013.01); *G01F 1/704* (2013.01); *G01F 1/74* (2013.01);
(Continued)

(58) Field of Classification Search
CPC .......... G06F 30/20; E21B 43/16; G01F 1/704; G01F 1/74; G06T 15/08; G01N 13/00; G01N 33/24
See application file for complete search history.

(56) References Cited

U.S. PATENT DOCUMENTS

| 3,818,757 A | 6/1974 | Brown |
| 4,498,134 A | 2/1985 | Hansen et al. |

(Continued)

FOREIGN PATENT DOCUMENTS

| CN | 101556687 | 10/2009 |
| CN | 102174888 | 9/2011 |

(Continued)

OTHER PUBLICATIONS

Jiang F, Tsuji T. Estimation of three-phase relative permeability by simulating fluid dynamics directly on rock-microstructure images. Water Resources Research. Jan. 2017;53(1):11-32. (Year: 2017).*

(Continued)

*Primary Examiner* — Chuen-Meei Gan
(74) *Attorney, Agent, or Firm* — Fish & Richardson P.C.

(57) ABSTRACT

Systems, methods, and computer program products can be used for visualizing the behavior of flow of two or more fluid phases, wherein a fluid phase behavior is represented in a visualization. One of the methods includes determining an occupation time, which is the amount of elapsed time from when a fluid phase first occupies a particular location until a second time. The method includes generating data for a visualization, with a location in the visualization corresponding to the particular location, and with the generated data for that location in the visualization indicating the occupation time.

19 Claims, 7 Drawing Sheets

Related U.S. Application Data

Figure 1:
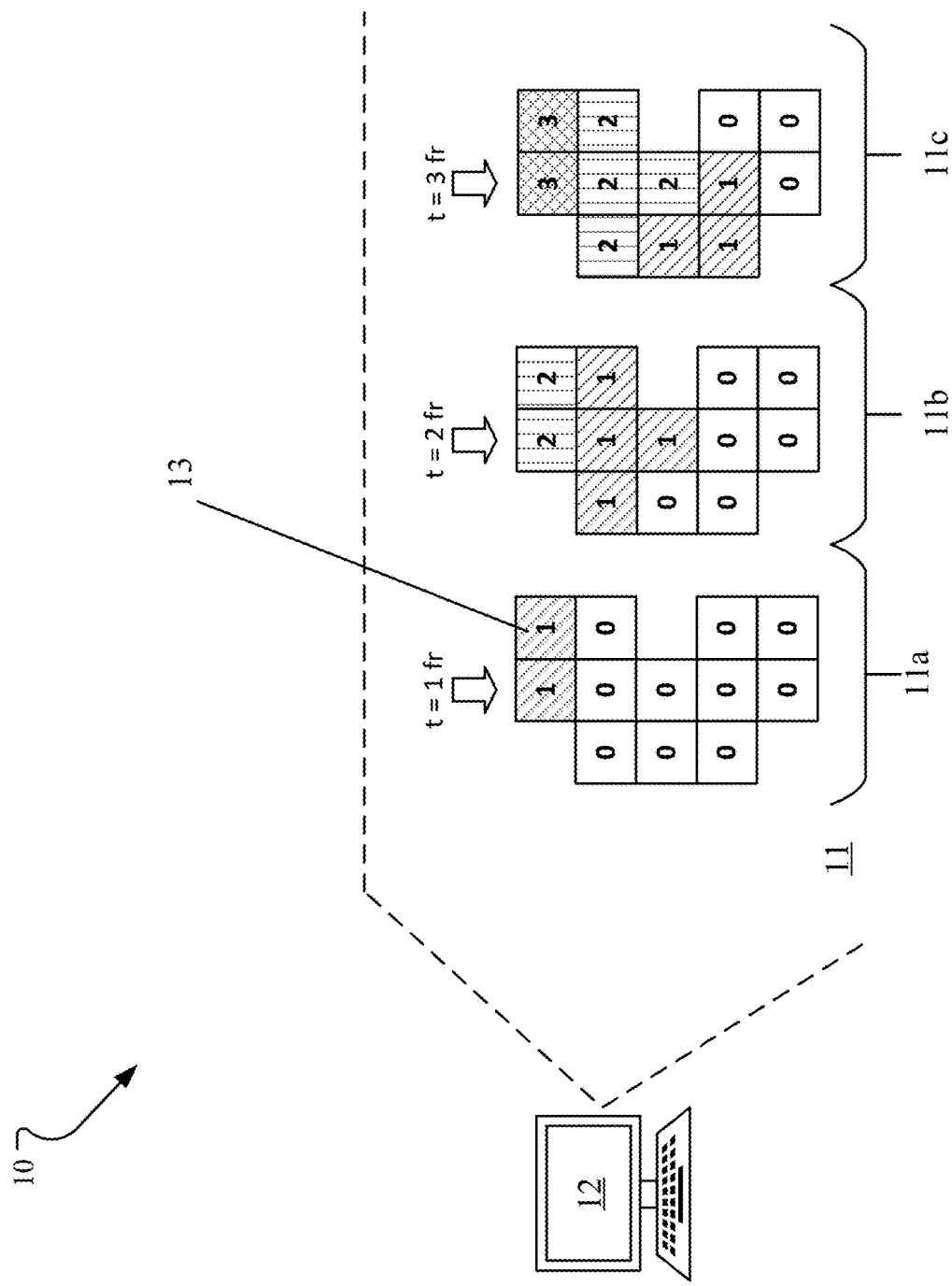

(60) Provisional application No. 62/450,989, filed on Jan. 26, 2017.

(51) Int. Cl.
  *G01F 1/704* (2006.01)
  *G01F 1/74* (2006.01)
  *G06T 15/08* (2011.01)
  *G01N 13/00* (2006.01)
  *G01N 33/24* (2006.01)

(52) U.S. Cl.
  CPC .............. *G06T 15/08* (2013.01); *G01N 13/00* (2013.01); *G01N 33/24* (2013.01)

(56) References Cited

U.S. PATENT DOCUMENTS

| | | |
|---|---|---|
| 4,507,726 A | 3/1985 | Grinberg et al. |
| 4,729,098 A | 3/1988 | Cline et al. |
| 4,809,202 A | 2/1989 | Wolfram |
| 4,831,519 A | 5/1989 | Morton |
| 4,860,245 A | 8/1989 | Kinoshita |
| 4,933,895 A | 6/1990 | Grinberg et al. |
| 4,969,116 A | 11/1990 | Wada et al. |
| 4,989,166 A | 1/1991 | Akasaka et al. |
| 5,038,302 A | 8/1991 | Kaufman |
| 5,069,065 A | 12/1991 | Sprunt et al. |
| 5,159,690 A | 10/1992 | Margolus |
| 5,255,212 A | 10/1993 | Kondoh et al. |
| 5,361,385 A | 11/1994 | Bakalash |
| 5,377,129 A | 12/1994 | Molvig et al. |
| 5,408,638 A | 4/1995 | Sagawa et al. |
| 5,416,729 A | 5/1995 | Leon et al. |
| 5,424,963 A | 6/1995 | Turner et al. |
| 5,432,718 A | 7/1995 | Molvig et al. |
| 5,442,733 A | 8/1995 | Kaufman et al. |
| 5,548,694 A | 8/1996 | Frisken Gibson |
| 5,594,671 A | 1/1997 | Chen et al. |
| 5,605,517 A | 2/1997 | Sherman |
| 5,606,517 A | 2/1997 | Traub et al. |
| 5,640,335 A | 6/1997 | Molvig et al. |
| 5,848,260 A | 12/1998 | Chen et al. |
| 5,953,239 A | 9/1999 | Teixeira et al. |
| 6,318,156 B1 | 11/2001 | Dutton et al. |
| 6,516,080 B1 | 2/2003 | Nur |
| 6,915,245 B1 | 7/2005 | Hinton et al. |
| 6,928,399 B1 | 8/2005 | Watts et al. |
| 7,209,873 B1 | 4/2007 | Kliegel |
| 7,590,514 B1 | 9/2009 | Olovsson |
| 8,583,411 B2 | 11/2013 | Fung |
| 8,757,871 B2 | 6/2014 | Gruebele et al. |
| 9,058,446 B2 | 6/2015 | Lu et al. |
| 9,228,873 B2 | 1/2016 | Crouse et al. |
| 9,507,047 B1 | 11/2016 | Dvorkin et al. |
| 10,101,188 B2 | 10/2018 | Crouse et al. |
| 10,550,690 B2 | 2/2020 | Crouse et al. |
| 10,762,252 B2 | 9/2020 | Gopalakrishnan et al. |
| 11,118,449 B2 | 9/2021 | Crouse et al. |
| 11,651,125 B2 | 5/2023 | Crouse et al. |
| 11,714,040 B2 | 8/2023 | Crouse et al. |
| 2002/0173915 A1 | 11/2002 | Egermann et al. |
| 2005/0182603 A1 | 8/2005 | Freitas et al. |
| 2006/0132131 A1 | 6/2006 | Fleury et al. |
| 2006/0277012 A1 | 12/2006 | Ricard et al. |
| 2007/0016389 A1 | 1/2007 | Ozgen |
| 2007/0112518 A1 | 5/2007 | Montaron |
| 2007/0276639 A1 | 11/2007 | Montaron et al. |
| 2008/0012853 A1 | 1/2008 | Geiger |
| 2008/0044543 A1 | 2/2008 | McClements et al. |
| 2009/0070085 A1 | 3/2009 | Gullapalli et al. |
| 2010/0030534 A1 | 2/2010 | Reich et al. |
| 2010/0128932 A1 | 5/2010 | Dvorkin et al. |
| 2010/0156901 A1 | 6/2010 | Park et al. |
| 2010/0274543 A1 | 10/2010 | Walker |
| 2010/0312535 A1 | 12/2010 | Chen et al. |
| 2011/0184711 A1 | 7/2011 | Altman et al. |
| 2011/0313744 A1 | 12/2011 | Oury et al. |
| 2012/0130639 A1 | 5/2012 | Hanson et al. |
| 2012/0136578 A1 | 5/2012 | Ghedan et al. |
| 2012/0179436 A1 | 7/2012 | Fung |
| 2012/0191432 A1 | 7/2012 | Khataniar et al. |
| 2012/0241149 A1 | 9/2012 | Chen et al. |
| 2012/0310614 A1 | 12/2012 | Beattie et al. |
| 2013/0018641 A1* | 1/2013 | Prisco ..................... G06F 30/20 702/47 |
| 2013/0080128 A1 | 3/2013 | Yang et al. |
| 2013/0116997 A1 | 5/2013 | Sun et al. |
| 2013/0151221 A1 | 6/2013 | Chen et al. |
| 2013/0317791 A1 | 11/2013 | Danielson |
| 2014/0019053 A1 | 1/2014 | de Prisco |
| 2014/0067347 A1 | 3/2014 | Gurpinar et al. |
| 2014/0343858 A1 | 11/2014 | Crouse et al. |
| 2015/0048007 A1 | 2/2015 | Weerasooriya et al. |
| 2015/0051892 A1 | 2/2015 | Carvajal et al. |
| 2015/0059447 A1 | 3/2015 | Rickards |
| 2015/0066463 A1 | 3/2015 | Shetty et al. |
| 2015/0141303 A1 | 5/2015 | Harwell et al. |
| 2015/0142407 A1 | 5/2015 | Wakefield et al. |
| 2015/0149139 A1 | 5/2015 | Chavez et al. |
| 2015/0268080 A1 | 9/2015 | Crouse et al. |
| 2016/0003010 A1 | 1/2016 | Fornel et al. |
| 2016/0188768 A1 | 6/2016 | Gopalakrishnan et al. |
| 2016/0209256 A1 | 7/2016 | Crouse et al. |
| 2016/0307359 A1 | 10/2016 | Desbrun et al. |
| 2017/0074770 A1 | 3/2017 | Fourno |
| 2017/0198573 A1 | 7/2017 | Kim et al. |
| 2018/0329112 A1 | 1/2018 | Lee et al. |
| 2018/0120213 A1 | 5/2018 | Dyshlyuk et al. |
| 2018/0253514 A1 | 9/2018 | Bryant et al. |
| 2019/0025461 A1 | 1/2019 | Wiener |
| 2019/0086250 A1* | 3/2019 | Crouse ................... G06F 30/20 |
| 2019/0154597 A1 | 5/2019 | Zhang |
| 2019/0186255 A1 | 6/2019 | Mustapha |
| 2019/0203593 A1 | 7/2019 | Fullmer et al. |
| 2019/0212241 A1 | 7/2019 | Crouse et al. |
| 2019/0368344 A1 | 12/2019 | Crouse et al. |
| 2020/0063532 A1 | 2/2020 | Crouse et al. |
| 2021/0062638 A1 | 3/2021 | Crouse et al. |
| 2021/0406434 A1 | 12/2021 | Gopalakrishnan et al. |
| 2022/0207219 A1 | 6/2022 | Otomo et al. |
| 2023/0077778 A1 | 3/2023 | Crouse et al. |
| 2023/0359794 A1 | 11/2023 | Crouse et al. |

FOREIGN PATENT DOCUMENTS

| | | |
|---|---|---|
| CN | 102245289 | 11/2011 |
| CN | 102472649 | 5/2012 |
| CN | 103698102 | 4/2014 |
| CN | 104067290 | 9/2014 |
| CN | 104334828 | 2/2015 |
| CN | 102383783 | 6/2015 |
| CN | 105393110 | 3/2016 |
| CN | 105580019 | 5/2016 |
| CN | 105910996 | 8/2016 |
| CN | 106233146 | 12/2016 |
| EP | 0228915 | 7/1987 |
| GB | 2066466 | 7/1981 |
| JP | 2011191848 | 9/2011 |
| JP | 2011525271 | 9/2011 |
| JP | 2016524222 | 8/2016 |
| WO | WO 1991017204 | 11/1991 |
| WO | WO 1992001993 | 2/1992 |
| WO | WO 1999034308 | 7/1999 |
| WO | WO 2008021652 | 2/2008 |
| WO | WO 2012071090 | 5/2012 |
| WO | WO 2016159807 | 10/2016 |
| WO | WO 2019097272 | 5/2019 |

OTHER PUBLICATIONS

U.S. Appl. No. 07/555,754, filed Jul. 12, 1990, Molvig.
U.S. Appl. No. 07/812,881, filed Dec. 20, 1991, Molvig.

(56) References Cited

OTHER PUBLICATIONS

Bao et al., "Lattice Boltzmann method for fluid simulations," Department of Mathematics, Courant Institute of Mathematical Sciences, New York University, Apr. 14, 2011, 44:1-16.
Bryant et al., "Prediction of relative permeability in simple porous media" Physical Review A vol. 46, No. 4 Aug. 15, 1992) (Year: 1992).
Burges et al., "Buoyant Mixtures of Cellular Automation Gases," Complex Systems, 1:31-50 (1987).
Catala, et al. "Fluid Flow Fundamentals." Oilfield Review, Dec. 31, 1996, 61-64.
Chatterjee et al., "A hybrid lattice Boltzmann model for solid-liquid phase transition in presence of fluid flow," Physics Letters A, Mar. 6, 2006, 351(4-5):359-367.
Chen & Ohashi, "The foundation and its application of the lattice Boltzmann method," Simulation, Nippon-Steel Technical Information Center, Ltd., Sep. 15, 1998, 17(3): 43-49 (with abstract).
Chen et al., "Lattice Boltzmann method for fluid flows," Annual review of fluid mechanics, Jan. 1998, 30(1):329-64.
Chen et al., "Lattice Boltzmann Model for Stimulation of Magnetohydordynamicis," Physical Review Letters, vol. 67,No. 27 (Dec. 1991), pp. 3776-3779.
Chopard et al., Cellular Automata Model for Heat Conduction in a Fluid, Physics Letters A, vol. 126, Nos. 8, 9, pp. 476-480 (Jan. 1988).
Clougueur et al., "RAPI, A Cellular Automaton Machine for Fluid Dynamics," Complex Systems, pp. 585-597 (1987).
CN Office Action in Chinese Appln. No. 201480049496.X; dated Dec. 18, 2017; 18 pages (with English translation).
CN Office Action in Chinese Appln. No. 201580021949.2, dated Aug. 10, 2018, 103 pages (with English translation).
CN Office Action in Chinese Appln. No. 201880014907.X, dated Mar. 3, 2020, 6 pages (with English Translation).
CN Office Action in Chinese Appln. No. 201880014907.X, dated Sep. 3, 2020, 13 pages (with English Translation).
Demianov et al., "Density Functional Modelling in Multiphase Compositional Hydrodyanmics" Canadian J. Chem. Engine., Apr. 2011. 89:206-26.
D'Humieres et al., "2-D and 3-D Hydrodynamics on Lattice Gases," Fruhjahrstagung der Schweiz. Physikalischen Gesellschaft, vol. 59 (1986).
D'Humieres et al., "Lattice Gas Models for 3D Hydrodynamics," 2 (4), pp. 291-297 (1986).
D'Humieres et al., Numerial Simulations of Hydrodynamics with Lattice Gas Automata in Two Dimensions, Complex Systems 1:599-632 (1987).
Dyn et al., "Optimizing 3D Triangulations Using Discrete Curvature Analysis," Mathematical Methods for Curves and Surfaces: Oslo Jan. 1, 2001, 1:135-146.
EP Extended European Search Report in EP Appln. No. 18744797.4, dated Dec. 5, 2019, 10 pages.
EP Supplemental European Search Report in European Appln. No. 18744797.4, dated Dec. 5, 2019, 39 pages.
Fredkin et al., "Conservative Logic." International Journal of Theoretical Physics, vol. 21, Nos. 3/4, pp. 219-253 (1982).
Frisch et al., "Lattice Gas Hydrodynamics in Two and Three Dimensions." Complex Systems 1:649-707 (1987).
Frisch et al., "Lattice-Gas Automata for the Navier-Stokes Equation," Physical Review Letters, vol. 56, No. 14, pp. 1505-1508 (Apr. 1986).
Ginzburg et al., "Analysis and improvement of Brinkman lattice Boltzmann schemes: Bulk, boundary, interface. Similarity and distinctness with finite elements in heterogeneous porous media" Physical Review, 2015, 91:023307-1-32.
Google Search Results, Jun. 28, 2021, 1 pp. (Year: 2021.
Hamedi et al., "Pore-scale investigation of phase distribution and residual-oil development during secondary and tertiary solvent injection," SPE Reservoir Evaluation & Engineering. Feb. 1, 2015, 18(01):39-52.
Han et al., "Modelling of thermal contact resistance within the framework of the thermal lattice Boltzmann method," International Journal of Thermal Sciences, Oct. 1, 2008, 47(10):1276-1283.
Hardy et al., "Molecular Dynamics of a Classical Lattice Gas: Transport Properties and Time Correlation Functions." Physical Review A, vol. 13, No. 5, pp. 1949-1961 (May 1976).
Hasslacher, Discrete Fluids: Part I: Background for Lattice Gas Automata, Los Alamos Science Special Issue, pp. 175-217 (1987).
Healy et al., "Status of Miscible Flooding Technology," 14th World Petroleum Congress, Jan. 1, 1994, 407-409.
Henon, "Isometric Collision Rules for the Four-Dimensional FCHC Lattice Gas," Complex Systems 1:475-494 (1987).
Hoshen & Kopelman, "Percolation and cluster distribution. I. Cluster multiple labeling technique and critical concentration algorithm," Physical Review B, Oct. 15, 1976, 14:8:3438-3445.
Huang et al.; "Shan-and-Chen Type Multiphase Lattice Boltzmann Study of Viscous Coupling Effects for Two-Phase Flow in Porour Media," International Journal for Numerical Methods in Fluids, Sep. 30, 2009; 61(3):341-354.
International Search Report and Written Opinion; PCT/US2018/015408; dated Mar. 12, 2018; 18 pages.
Jiang et al., "Estimation of three-phase relative permeability by simulating fluid dynamics directly on rock-microstructure images," Jan. 5, 2017, 22 pages.
Kadanoff et al., "Transport Coefficients Near the Critical Point: A Master Equation Approach," 165 Phys. Review 310 (1968).
Kadanoff, "On Two Levels" Physics Today (Sep. 1986).
Karsch, "Lattice simulations of the thermodynamics of strongly interacting elementary particles and the exploration of new phases of matter in relativistic heavy ion collisions," InJournal of Physics: Conference Series 2006 , 46(1):122-131.
Kaufman et al."Volume Graphics." IEEE, Jul. 1993, pp. 51-64.
Klein, "Negative Absolute Temperatures." Physical Review, vol. 104, No. 3, p. 589 (Nov. 1956).
Kovscek et al., "A Pore-Leval Scenario for the Development of Mixed-Wettability in Oil Reservoirs," Earth Science Division of Lawrence Berkeley Laboratory and Department of Chemical Engineering, prepared for U.S. Department of Energy, Sep. 1992, 1-58.
Krummel et al. "Visualizing Multiphase Flow and Trapped Fluid Configurations in a Model Three-Dimensional Porous Medium" (Year: 2013).
Ladd et al., "Lattice-Boltzmann simulations of particle-fluid suspensions," Journal of statistical physics, Sep. 1, 2001, 104(5-6):1191-251.
Lee et al. "A stable discretization of the lattice Boltzmann equation for simulation of incompressible two-phase flows at high density ratio," Journal of Computational Physics, Jun. 10, 2005, 206(1):16-47.
Lenormand et al., "Physics of Blob Displacement in a Two-Dimensional Porous Medium," Mar. 1988, SPE Formation Evaluation, pp. 271-275.
Li et al. "GPU-based numerical simulation of multi-phase flow in porous media using multiple-relaxation-time lattice Boltzmann method" (Year: 2013).
Li et al., "Upscaled Lattice Boltzmann Method for Simulations of Flows in Heterogeneous Porous Media," Geofluids, Feb. 2017, 2017:1-12.
Lin et al., "Plasma Simulation Using the Massively Parallel Processor," NASA CP-2478, pp. 185-191 (Jul. 1987).
Man et al., "Pore Network Modelling of Electrical Resistivity and Capillary Pressure Characteristics", Transport in Porous Media, Dec. 2000, 41(3):263-285.
Margolus et al., "Cellular-Automata Supercomputers for Fluid-Dynamics Modeling." Physical Review Letters, vol. 56, No. 16, pp. 1694-1696 (Apr. 1986).
Martys et al., "Multiscale modeling of fluid transport in heterogeneous materials using discrete Boltzmann methods," Materials and Structures, Dec. 2002, 35:650-9.
Mohammdmoradi et al., "Petrophysical Characterization of Porous Media Starting from Micro-Tomographic Images", Advances in Water Resources, May 2016, 35 pages.
Mohanty et al., Physics of Oil Entrapment in Water-Wet Rock, Feb. 1987, SPE Reservoir Engineering, pp. 113-128 (Year: 1987).

(56) References Cited

OTHER PUBLICATIONS

Molvig et al., "Fluid CAD That Challenges Computational Fluid Dynamics," Machine Design, Dec. 1994, 66(23):96-8.
Molvig et al., "Multi-species Lattice-Gas Automata for Realistic Fluid Dynamics," Springer Proceedings in Physics, vol. 46, pp. 206-231 (1990) (abstract only).
Molvig et al., "Removing the Discreteness Artifacts in 3D Lattice-Gas Fluids", Proceedings of the Workshop on Discrete Kinetic Theory, Lattice Gas Dynamics, and Foundations of Hydrodynamics, World Scientific Publishing Co., Pte., Ltd., Singapore (1989).
Motealleh et al., "Unified Model of Drainage and Imbibition in 3D Fractionally Wet Porous Media" Transport in Porous Media, Jul. 2013, 99(3):581-611.
One Petro Search Results, Jan. 26, 2021, 11 pp. (Year: 2021).
PCT International Search Report and Written Opinion, in International Appln. No. PCT/US2018/015408, dated Mar. 12, 2018, 6 pages.
Pepiot et al., "Numerical analysis of the dynamics of two- and three-dimensional fluidized bed reactors using an Euler-Lagrange approach," Powder Technology, Apr. 1, 2012, 220: 104-121.
Pereira, "Fluid Flow, Relative Permeabilities and Capillary Pressure Curves Through Heterogeneous Porous Media," Applied Mathematical Modelling, May 31, 2019, vol. 75, p. 481-493.
Perez et al., "OUPPI-1, ASIMD Computer Using Integrated Parallel Processors." Proc. of Compar Conf. Papers Plenary Sess. and Stream A Manchester, Sep. 12-16, 1988, British Comp. Soc. Parallel Proc. Spec. Group GB.
Petkov et al., "Efficient LBM visual simulation on face-centered cubic lattices," IEEE Transactions on Visualization and Computer Graphics, Feb. 27, 2009, 15(5):802-14.
petrowiki.org/Miscible_flooding [online] "Miscible flooding" Aug. 19, 2013, retrieved on Oct. 10, 2019, retrieved from URL <https://petrowiki.org/Miscible flooding>, 9 pages.
Prodanovic et al., "Investigating Matrix-Fracture Transfer via a Level Set Method for Drainage and Imbibition"; SPE Journal, vol. 15, No. 01; Mar. 1, 2010; 17 pages.
Prodanovic et al., "Physics-Driven Interface Modeling for Drainage and Imbibition in Fractures," Sep. 2009 SPE Journal, pp. 532-542 (Year: 2009).
Qian et al., "Lattice BGK Models for Navier-Stokes Equation." Europhysics Letters, 17(6):479-484 (1992).
Raabe, "Overview of the lattice Boltzmann method for nano-and microscale fluid dynamics in materials science and engineering," Modelling and Simulation in Materials Science and Engineering, Sep. 16, 2004, 12(6):R13-R46.
Ramsey, "Thermodynamics and Statistical Mechanics at Negative Absolute Temperatures." Physical Review, vol. 103, No. 1, pp. 20-28 (Jul. 1956).
Ramstad et al., "Relative Permeability Calculations from Two-Phase Flow Simulations Directly on Digital Images of Porous Rocks" Transp Porous Med (2012) 94:487-504 (Year: 2012).
Ramstad et al., "Simulation of two-phase flow in reservoir rocks using a lattice Boltzmann method," Spe Journal, Dec. 1, 2010, 15(04):917-27.
Rivet, "Three-Dimensional Lattice Gas Hydrodynamical Simulations: First Results." C.R. Acad. Sci. Paris, t. 305, Series II, pp. 751-756 (1987).
Rosenblum, "Photorealistic Terrain Imaging and Flight Simulation," IEEE, 1994 pp. 10-12.
Sheng et al., "Numerical Prediction of Relative Permeability from MicroCT Images: Comparison of Steady-State versus Displacement Methods," Oct. 30-Nov. 2, 2011, SPE Annual Technical Conference and Exhibition, Denver, Colorado, 16 pages.
Sohrabi et al., "Novel Insights into the Pore-scale Mechanisms of Enhanced Oil Recovery by CO2 Injection," 74th EAGE Conference and Exhibition, Jun. 4, 2012, 154529:1-14.
Sohrabi et al., "Visualisation of residual oil recovery by near-miscible gas and SWAG injection using high-pressure micromodels," Transport in Porous Media, Sep. 1, 2008, 74(2):239-57.
Suhrer et al., "Upscaling Method for Obtaining Primary Drainage Capillary Pressure and Resistivity Index with Digital Rock Physics," IPTC-20035-ABSTRACT, 2020, 13 pages.
Teixeira, "Continuum Limit of Lattice Gas Fluid Dynamics." B.A. Sc. Engineering Science University of Toronto (1988).
Toffoli, "Cellular Automata as an Alternative to (Rather Than an Approximation of) Differentiation Equation in Modeling Physics." Physica 10D: 117-127 (1984).
Tsuji et al., "Characterization of immiscible fluid displacement processes with various capillary numbers and viscosity ratios in 3D natural sandstone," Advances in Water Resources, Sep. 1, 2016, 95:3-15.
Tucker, "Cellular Automata Machine: The Ultimate Parallel Computer," High Technology, pp. 85-87 (Jun. 1984).
Van Den Pijl, "Computation of bubbly flows with a mass-conserving level-set method," Dissertation at Delft University of Technology, Nov. 22, 2005, 139 pages.
Vichniac, "Cellular-Automata Fluids." Instabilities and Nonequilibrium Structures II, pp. 97-116 (1989).
Vichniac, "Stimulating Physics with Cellular Automata." Physica, 10D:96-110, 1984 (abstract only).
Wijk et al., "Three Ways to Show 3D Fluid Flow" IEEE Computer Graphics and Applications, Sep. 1994, 14(5):33-9.
Wolfram, "Cellular Automation Fluids 1: Basic Theory," J. Stat. Phys., vol. 45, Nos. 3/4, pp. 471-526 (1986).
Xu et al., "Continuous vs Discontinuous Capillary Desaturation and Implications for IOR/EOR," InPaper SCA2018-066 presented at the International Symposium of the Society of Core Analysts held in Trondheim, Norway, Aug. 2018, 1-10.
Yiotis et al., "Blob population dynamics during immiscible two-phase flows in reconstructed porous media," Physical Review E, Mar. 4, 2013, 87(3):1-12.
Zhang et al., "Single Component, Multiphase Fluids Flow Simulation in Porous Media with Lattice Boltzmann Method" 2012 Fourth International Conference on Computational and Information Sciences (Year: 2012).
Zhu et al., "Extending a Gray Lattice Boltzmann Model for Simulating Fluid Flow in Multi-Scale Porous Media," Sci. Rep., Apr. 2018, 8(5826):1-19.
CN Office Action in Chinese Appln. No. 201980012848.7, dated Feb. 1, 2023, 27 pages (with English translation).
Dixit et al., "Pore-scale modeling of wettability effects and their influence on oil recovery," SPE Reservoir Evaluation & Engineering, Feb. 1999, 2(1) 25-36.
EP Office Action in Europe Appln. No. 19738994.3, dated Sep. 21, 2022, 11 pages.
JP Office Action in Japanese Appln. No. 2020538656, dated Dec. 5, 2022, 16 pages (with English translation).
Morgan, et al., "A Parametric Investigation of Oblique Shockwave/Turbulent Boundary Layer Interaction Using LES," 41st AIAA Fluid Dynamics Conference and Exhibit, Jun. 2011, pp. 1-19.
U.S. Appl. No. 18/317,473, Crouse et al., filed May 15, 2023.
Office Action in Japanese Appln. No. 2020-538656, dated Jul. 21, 2023, 6 pages (with English translation).

* cited by examiner

MULTI-PHASE FLOW VISUALIZATIONS BASED ON FLUID OCCUPATION TIME

CLAIM OF PRIORITY

This application claims priority under 35 USC § 119(e) to U.S. Provisional Patent Application Ser. No. 62/450,989, filed on Jan. 26, 2017, the entire contents of which are hereby incorporated by reference.

BACKGROUND

Multi-phase or multi-component (from herein called: multiphase) flow is widespread in many engineering disciplines. In some cases, the geometry which defines the boundaries confining the multiphase flow are known precisely, such as a system of pipes or channels. Other scenarios involve highly random and complex geometry, such as the pore space network of a porous rock. One exemplary application of multiphase flow through such complex porous media is the study of oil and water flow in oil reservoir rock. A key property of this flow behavior is the "relative permeability" of each fluid phase, which characterizes how easily that phase moves through the rock for the specified conditions.

SUMMARY

In general, one innovative aspect of the subject matter described in this specification can be embodied in methods for the behavior of flow of two or more fluid phases, wherein a fluid phase behavior is represented in a visualization. The methods include the act of determining an occupation time, which is the amount of elapsed time from when a fluid phase first occupies a particular location until a second time. The methods also include the act of generating data for a visualization, with a location in the visualization corresponding to the particular location, and with the generated data for that location in the visualization indicating the occupation time.

Other embodiments of this aspect include corresponding computer systems, apparatus, and computer programs recorded on one or more computer storage devices, each configured to perform the actions of the methods. A system of one or more computers can be configured to perform particular actions by virtue of having software, firmware, hardware, or a combination of them installed on the system that in operation causes or cause the system to perform the actions. One or more computer programs can be configured to perform particular actions by virtue of including instructions that, when executed by data processing apparatus, cause the apparatus to perform the actions.

The foregoing and other embodiments can each optionally include one or more of the following features, alone or in combination. The visualization of the fluid phase may include assigning a color based on the occupation time. The methods may include the act of at a third time subsequent to the second time, updating the occupation time to be the difference between the third time and the first, and updating the visualization based on the update occupation time. Locations in the visualizations associated with smaller amounts of occupation time, relative to other amounts of occupation time of other locations in the visualization, may be represented as a displacement front. The fluid phase may be a displacing phase, and locations with decreased amounts of occupation time, relative to other amounts of occupation time of other locations, may represent a displacement front.

The methods may also include the act generating data for rendering a visualization of the displacement front. A fluid phase may be a water based or gas based fluid phase. The second time may be a current time. The location may be a location within or around a porous medium. The porous medium may be a rock. One of the two or more fluid phases may represent an oil based fluid phase. The location may be specified in a data set or in an image. The methods may include the acts of simulating, in a simulation space, flow of two or more fluid phases in a physical media. The visualization may be a visualization of simulation results. The location in the visualization may be a voxel, wherein each voxel in the visualization may be colored, and wherein a color of a particular voxel may be set according to the occupation time. The methods may include the act of rendering the visualization. The visualization may be included in a video or in a set of visualizations. The location in the visualization may represent a surface location.

The details of one or more embodiments of the subject matter of this specification are set forth in the accompanying drawings and the description below. Other features, aspects, and advantages of the subject matter will become apparent from the description, the drawings, and the claims.

DESCRIPTION

An especially important aspect of the relative permeability of oil/water flow in porous rock is the displacement behavior due to water flood when water pushes oil out of the rock. As for many engineering applications, the transition between two conditions is often the objective of experimental lab testing or numerical testing approaches. The rock sample is initially filled with oil. During the water flood, water is injected into the rock core and pushes oil out. The displacement process is highly complex and depends on many parameters, such as the pore space topology, viscosity ratio, Capillary number. The displacement through film growth competes with piston-like displacement (bulk pore volumes). Wettability plays another important role in the displacement dynamics.

The desire to optimize oil production and to minimize residual oil demands to fully understand and eventually control the displacement mechanism.

High fidelity computer simulation of flow in porous rock has recently become feasible due to advances in imaging, numerical methods, and high performance computing. The ability to perform multiphase flow simulations to accurately predict relative permeability for a reservoir rock sample is an active area of research and commercial interest. The approach of interest here involves first performing 3D imaging of the porous rock to generate a digital representation, followed by image analysis to determine the geometry of the pore space network, and then numerical multiphase flow simulation for various saturation values to obtain predictions of flow behavior including relative permeability as a function of saturation. The flow simulation results can also be used to understand the details of the pore-scale multiphase flow dynamics which may provide insight suggesting approaches for how to modify the relative permeability vs saturation curve.

In one example, pore-scale multiphase fluid flow simulation results are used to understand the fluid displacement mechanisms in reservoir rock. Time dependent visualization is developed to give insight into the fluid-fluid interface movement at different values of a capillary number. Generally, a capillary number is a ratio of viscous to interfacial tension forces, usually expressed as $Ca=V*U/I$, where V=viscosity, U=velocity and I=interfacial tension. The flow simulations use a multi-phase lattice-Boltzmann method. Micro-CT images of Fontainebleau rock are used to construct the geometry used as input to the simulations. A flow rate is controlled to achieve a specified capillary number (for example 1e-5), where typically one of the fluids is chosen as the reference fluid for determining viscosity and velocity values. A visualization technique is applied to the results, in which one fluid phase (for example water) is given a color indicating local occupation time to highlight interface movement and help visually capture capillary events, i.e., fluid dynamics behavior occurring at the pore scale and driven by capillary forces. In some implementations, other visual indicators of occupation time can be used. For example, opacity, texture, etc.

Generally, a capillary force includes a force caused by interfacial tension, particularly important when there is a large surface to volume ratio; forces responsible for capillary action only occur when multiple fluid phases and a surface are present. Generally, pore-scale includes a scale of individual pores within a pore space of a porous material. Generally, when the surface attracts one phase more strongly than the other, they are referred to as the wetting phase and non-wetting phase. Generally, capillary events include snap-off of the non-wetting phase, retraction of the non-wetting phase, corner flow of the wetting phase, film swelling of the wetting phase, and Haines jumps.

The following describes an example occupancy time visualization. A clear difference of the water front shape (displacement front) is observed under different capillary number condition. With visualization of the water phase using the present invention, it is clearly seen that the fluid interface advancing speed varies with pore cross-section area and shape, where the fluid interface advancing speed indicates a speed of the leading interface when one phase is pushing another phase forward. Different fluid mechanisms in multiphase dynamic displacement under different capillary numbers are observed. The new visualization approach is able to capture interface movement and help understand pore-scale multiphase events.

One important aspect of simulating imbibition or drainage relative permeability simulations is to provide the ability to understanding the displacement process in great detail with the goal of better controlling the displacement and finally optimizing oil production. Some of the key questions are: How does water displace oil? Where does it go first? Why does it prefer a certain displacement path over another? To better analyze and understand the displacement process, each voxel in pore space obtains a new quantity which reflects the age of water or the age of oil assuming that a voxel can be marked as water or oil. In general, a voxel can be thought of as a representation of a particular location in the pore space. At a time, the voxel may be occupied by water, oil, or a combination of water and oil. As used herein, a voxel (location in pore space) that is occupied predominately by oil is referred to as an oil voxel, a voxel (location in pore space) that is occupied predominately by water is referred to as a water voxel. The age of the phase represents the amount of time passed from when a fluid phase first occupied a location.

For simplicity, the age of water will be explained. Modeling the age of oil can be performed using an analogous process. Initially, the pore space of the digital rock is filled with oil and some initial water. For all voxels (representing water and oil) the corresponding quantity to describe the age of water (from here on called: age) is set to 0. It is possible to distinguish between initial water and injected water. In some implementations, the age of injected water may be tracked separately from the age of initial water. In some implementations, the age of injected water and initial water are not tracked separately. As water is injected into the pore space, some oil voxels will change the property from oil to water (descriptively becoming water voxels). When that happens, the water age is set to 1. As the simulation continues, the age of each water voxel is incremented by a well-defined increment. For example, the water age is incremented by one each time a new measurement frame is written. A measurement frame may represent the passage of a predetermined amount of time. At a time during the simulation, it is possible to clearly identify the displacement front by filtering all voxels which have a water age of 1. Generally, a displacement front includes locations in the visualizations associated with least amounts of elapsed time. In cases where oil displaces local water, the age is reset to 0 or the predefined value for representing oil. It is also possible to filter pores (or pore voxels) which were water displaced before or after a certain time. So, in addition to a typical analysis where the oil-water distribution in pore space is analyzed, it is also possible to show locations in pore space where water was able to displace oil at a specific time in the past.

Referring to FIG. 1, diagram 10 illustrates results 11 of an example execution, by a data processing system 12, of the algorithm (e.g., an aging algorithm) described above. The cells (e.g., cell 13) indicate voxels of a pore space. At t=1 frame (portion 11a of results 11), the top two voxels are incremented because the voxels changed their property from oil to water going from frame 0 to frame 1. The t=2 frame (portion 11b of results 11) shows that the displacement front progressed by one voxel at frame 2. The voxels where the age was set to 1 in frame 1 are now incremented to 2. The t=3 frame (portion 11c of results 11) shows another frame where the displacement front has further progressed.

Figure 2A:
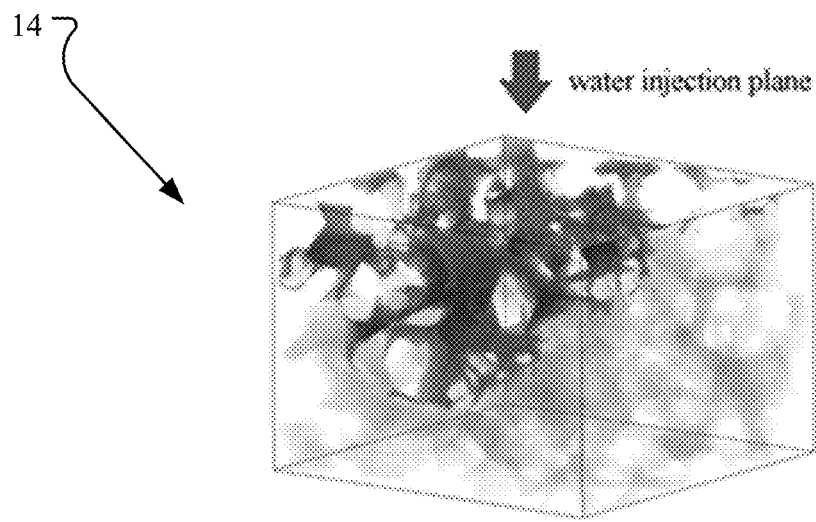
Figure 2B:
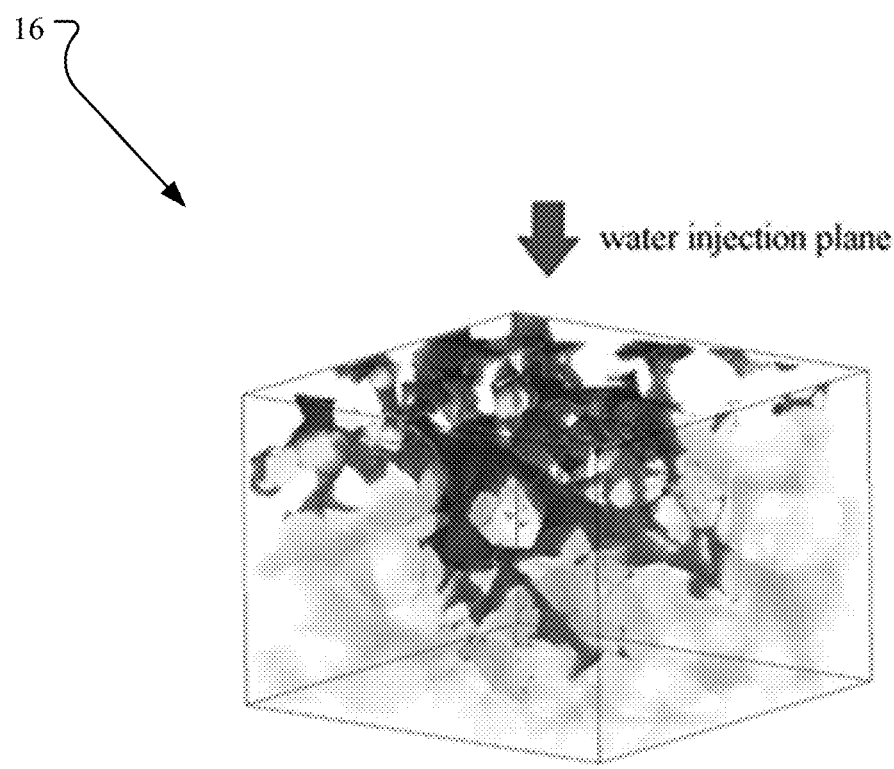

FIGS. 2A and 2B are each a visualization of the fluid phases within the pore space. Referring to FIG. 2A, diagram 14 illustrates a comparison of the displacement of oil through water-flood for capillary number, Ca=1e-4, at a water saturation of exactly 24%. Referring to FIG. 2B, diagram 16 illustrates a comparison of the displacement of oil through water-flood for capillary number, Ca=1e-5, at a water saturation of exactly 24%. Both fluid phases, oil and water, can be visualized as in FIGS. 2A and 2B using a spectrum of colors, opacity, shading, and/or texture to indicate the fluid phase of the voxel and the age of that phase. Accordingly, the volume is rendered with different opacity values, colors, and shading. In this example, oil is shown as the lighter shading and water is shown using darker shading. Other colors can be used, for example, oil can be shown in orange and can have a lower opacity compared to water. In one example, the color of water can range from purple to light blue. Purple can represent young water that has only recently displaced the oil in the location represented by the voxel, the displacement front, while light blue is old water and shows locations which were displaced by water far earlier in the simulation. Generally, a water injection plane is a top surface of a volume shown in each of diagrams 14, 16.

Figure 3A:
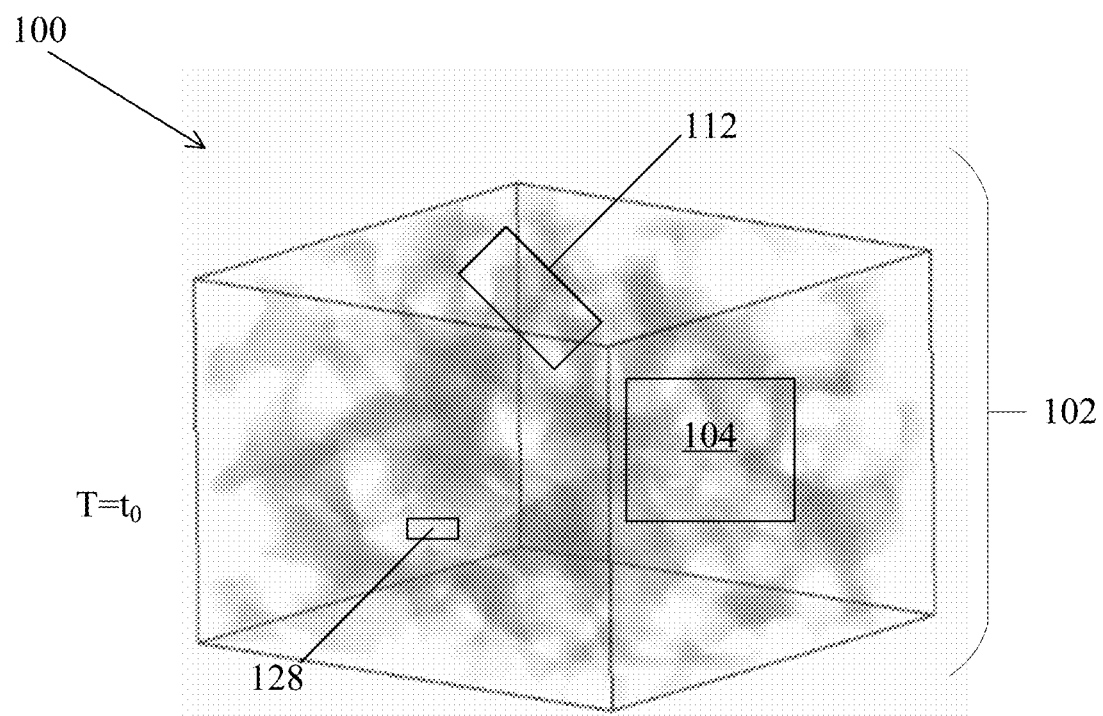

Referring to FIG. 3A, diagram 100 illustrates visualization 102. In this example, visualization 102 is a visualization of a volume (e.g., a porous media such as a rock sample) that includes a fluid phase, e.g., oil, at a particular time or at an initial/starting time T, denoted as $T=t_0$. A data processing system generates visualization 102 (and the other visualizations described herein) by processing data sets that specify coordinates of a particular location (e.g., a location in a porous media, a location in a rock sample, a location in a simulation space of a simulation, and so forth) and an attribute of that location (e.g., presence of oil, water, oil and water, or an absence of a fluid phase) at a particular time. In this example, the data sets include a plurality of records, with each record specifying coordinates for a particular location and an attribute of that location at a particular time. As described herein, these data sets are generated from results of performing simulations, from performing an X-ray of a physical media, from analyzing an image or from performing other imaging modalities on a physical media (e.g., a rock sample). Based on the processed data set, the data processing system generates or reconstructs visualizations of the locations represented in the data set. This reconstructed visualization includes a plurality of locations in the visualization, with each location in the visualization corresponding to a location in the data set. The data processing system sets a color for each location (e.g., voxel) in the visualization based on a mapping between various time or aging thresholds and various colors, opacity, textures, shading, etc.

In another example, visualization 102 is a visualization of a pore space that includes oil. In this example, visualization 102 shows where oil is in the pore space by coloring or shading portions of visualization 102 to represent the oil. For example, locations 104, 112, 128 (or a portion of locations 104, 112, 128, respectively) of visualization 102 are shaded to represent the oil. In this example, each of locations 104, 112, 128 corresponds to a location specified in a data set (e.g., a data set of simulation results, an image data set generated by performing X-rays on porous media, and so forth). Generally, a correspondence includes a mapping of one location to another location, of one item of data to another item of data and so forth.

Figure 3B:
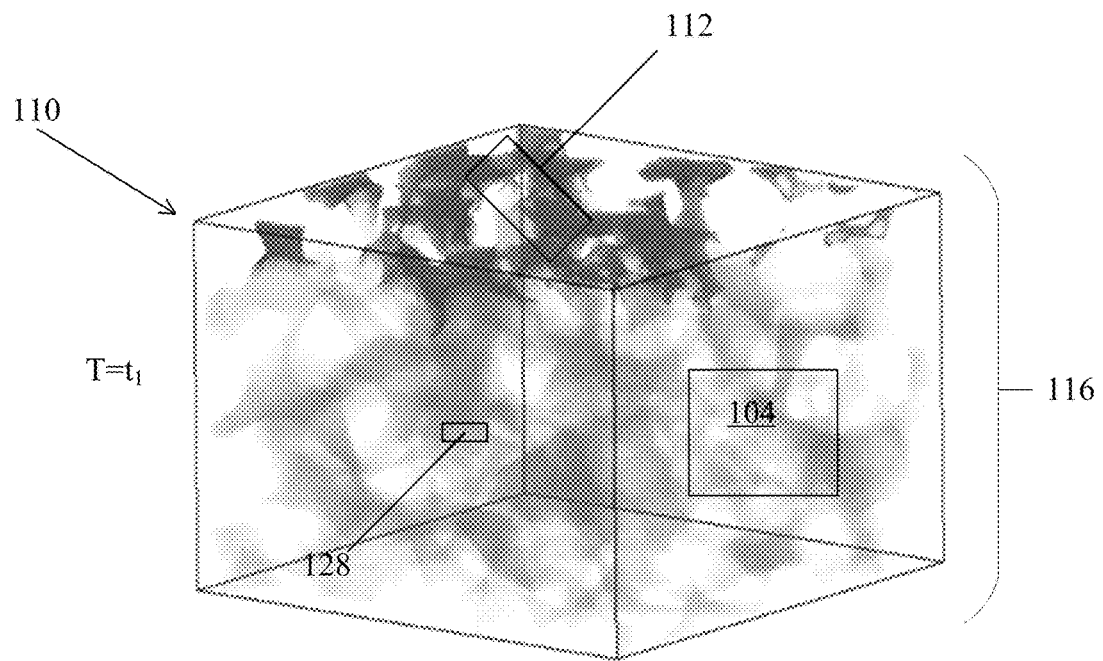

Referring to FIG. 3B, diagram 110 illustrates visualization 116 of the volume at a time that is subsequent to $T=t_0$. This subsequent time is denoted as $T=t_1$. In this example, visualization 116 is a variation of visualization 102, e.g., by updating visualization 102 to account for the introduction of another fluid phase (e.g., water) into the pore space. Color of location 112 in visualization 116 is shaded to represent an amount of elapsed time from when water occupied a location corresponding to location 112 at a first time (e.g., an initial time or $T=t_0$) until another time, e.g., a current time or $T=t_1$. In this example, the shading in location 112 represents new water in a location of a physical media (e.g., a rock sample), an image or a simulation. Generally, new water includes water that has occupied a location for more than a threshold period of time, e.g., a new water threshold period of time, but less than another, longer threshold period of time (e.g., an old water threshold period of time, as described below). In this example, the coloring of locations 104, 128 in visualization 116 remain the same and do not change, thereby representing that at time $T=t_1$ water has not yet entered the locations (e.g., the physical locations or the locations in a simulation) corresponding to locations 104, 128.

Figure 3C:
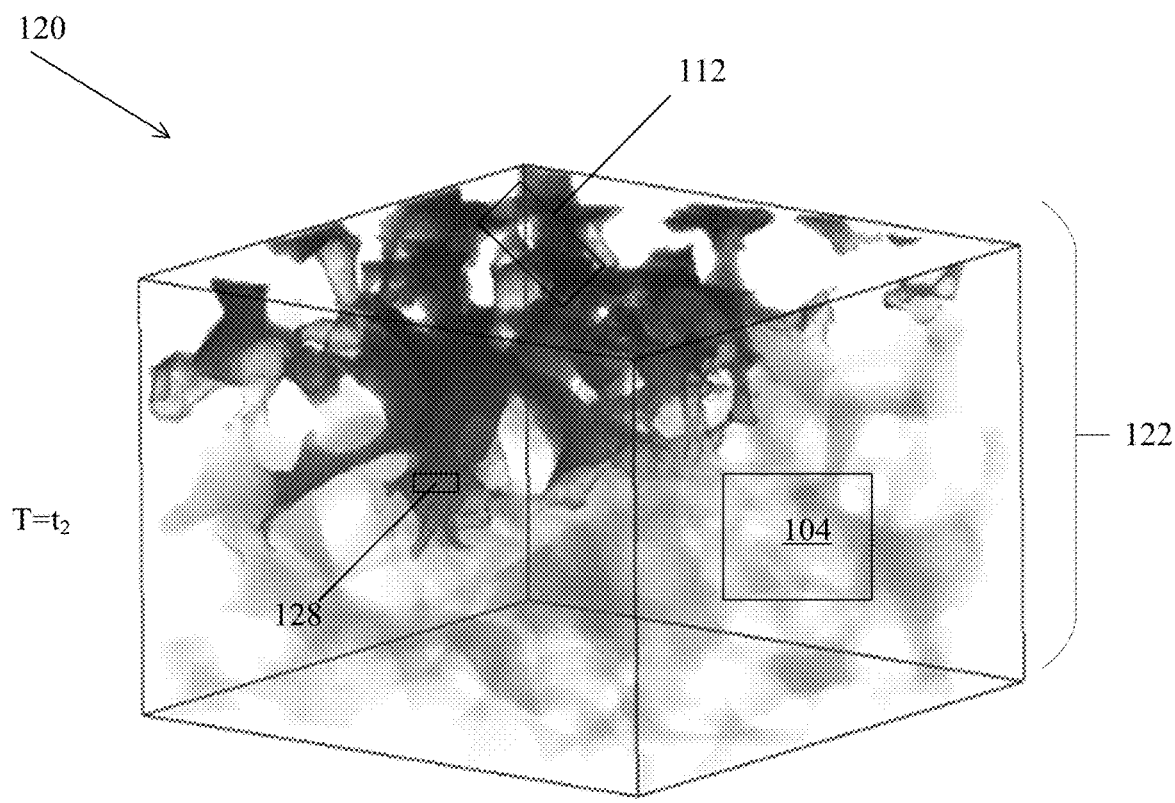

Referring to FIG. 3C, diagram 120 illustrates visualization 122 of the volume at a time that is subsequent to $T=t_1$. This subsequent time is denoted as $T=t_2$. In this example, visualization 122 is a variation of visualization 1116, e.g., by updating visualization 116 to account for the introduction of more of the other fluid phase (e.g., water) into the pore space. Color of location 112 in visualization 122 is darkly shaded (other colors can be used such as a dark blue (or mostly dark blue), to represent an amount of elapsed time from when water occupied a location corresponding to location 112 at a first time (e.g., an initial time or $T=t_0$) until $T=t_2$). In this example, the dark blue color in location 112 represents old water, at $T=t_2$, in a location of a physical media (e.g., a rock sample), an image or a simulation that corresponds to location 112. Generally, old water includes water that has occupied a location for more than a threshold period of time, e.g., an old water threshold period of time. In this example, the coloring of location 128 in visualization 122 is changed to represent that water has entered the location (e.g., in the physical media) corresponding to location 128. The coloring of location 128 specifies that the water in the physical location corresponding to location 128 is new water. The coloring of location 104 in visualization 122 remains unchanged (relative to visualizations 102, 116), thereby representing that at time $T=t_2$ water has not yet entered the location (e.g., the physical location or the location in a simulation) corresponding to location 104.

As indicated earlier, many more scenarios can be investigated using the proposed aging process, by defining new quantities which reflect the age of a property or the age of a variation of the property, as shown below.

Tracking of the age of a density variation: Often, a quantity undergoes a slow change in time. For example, the transition of an oil voxel to a water voxel can take many frames. In each frame, a small amount of the oil density is reduced while the water density is increased. This may happen for a very slow moving slug, for a growth of a water film and many other possible scenarios. In this case the algorithm may be modified in the following way. Every density change is assigned a certain duration for which the density is visualized, for example 100 frames. For example, if the water density changes by 10% between certain 2 frames, that density variation can be weighted in such a way that the density contribution can be identified for the next 100 frames. The weight can be either constant or it can decay over time, e.g. over 100 frames. In that case, the "aging density variation" could be defined as: rho_delta_age=weight(t)*delta_rho where the weight is decaying with time, e.g. is reduced by 10% between 2 frames. That way, small, but important density changes can be visualized in a competitive way of bulk fluid displacement.

Another implementation can include tracking the age of a fluid touching a surface. For example, a system can model a typical aging process to restore a rock sample's wettability. In general, wettability is the tendency of one fluid to spread on, or adhere to, a solid surface in the presence of other fluids. For example, a water-wet rock sample can be initially filled with 100% water and then drained with oil. This has the ability to alter the wetting behavior of the surface of the rock. Initially, all surface elements are attributed to be water-wet. Once the property of voxels which are close enough to surface elements so that the surface elements is exposed to the oil-wet character of the oil voxel, the surface element undergoes an alteration of wetting behavior. Over time, the water-wet character of the surface element transforms into an oil-wet character. Once the surface element is exposed to the oil voxel, the surface element is assigned an age. The change of wettability from water-wet to oil-wet can be determined as a function of the age of the oil contact.

In general, a quantity (e.g. velocity, pressure, Atwood Number, and so forth) can be assigned, e.g., by the data processing system, an age and can undergo a corresponding analysis. Furthermore, derivatives of the change of quantities can be assigned an age and correspondingly tracked. For example, the detection of convergence may be a function of the speed a certain quantity changes—so, for example, the question may not be whether the difference of the velocity is below a certain threshold between two frames, but the question may be whether the change of the difference of the velocity between two frames change. The history of velocity change may be part of the convergence criterion.

Figure 4:
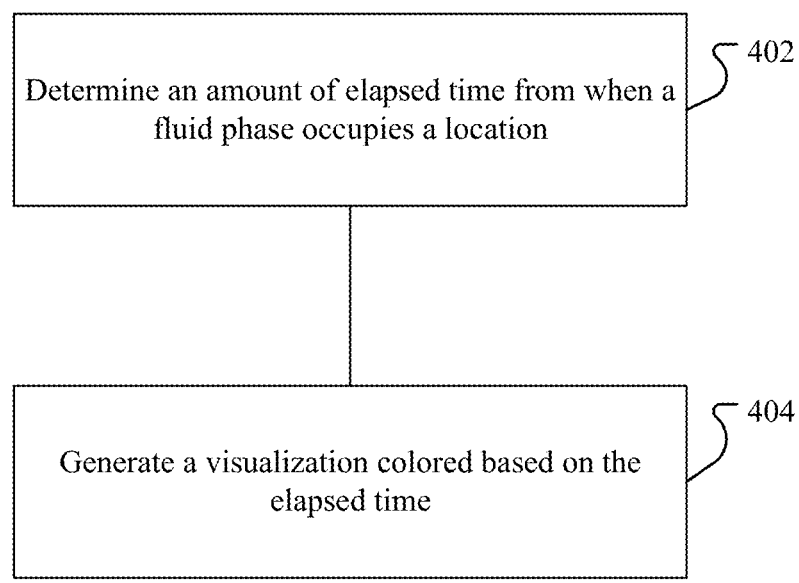

FIG. 4 is a flowchart of an exemplary process 400, executed by a data processing system, for visualizing the flow of two or more fluid phases. Examples of fluid phases include hydrocarbon (or oil) and brine (or water). The process 400 may be performed by a data processing system that is configured to process instructions stored on a non-transitory computer readable medium.

The process 400 determines 402 an amount of elapsed time from when a fluid phase occupies a particular location (e.g., specified in a data set, of a porous media or rock sample, and so forth) at a first time until a second time. In some implementations, the first time may represent the time when the fluid phase first occupies the particular location. For example, the time that water first occupies a particular location. As described above, the fluid phase may be identified by looking at the fluid density of the location. At the time when the fluid density is crosses a particular threshold (indicating that the fluid in the location is predominately water) the process 400 identifies the time as the first time. In some implementations, the second time is the current time. In some implementations, the second time may be represented by frames in a fluid flow simulation. The amount of time can be determined based on a data set that specifies coordinates of a location of a fluid phase at a particular time, or can be determined based on a simulation of the flow of two or more fluid phases in a physical media. The data set can be based on images where the particular location is a location within the images. The data set can be a 4 dimensional data set.

The data processing system generates 404 data for a visualization. A location in the visualization corresponds to the particular location. The location in the visualization is colored with a color, selected from a set of colors, that represents the amount of elapsed time from then the fluid phase occupies the particular location at the first time until the second time.

The colors may be determined by the data processing according to a set of rules that specify a mapping between an amount of elapsed time and a color. For example, the colors can be selected by the data processing system according rules in a rule set, represented by the chart below:

| Elapsed Time | Color |
|---|---|
| 1-5 seconds | Purple |
| 6-15 seconds | Blue |
| <15 seconds | Light Blue |

In some implementations, a color may be used to represent locations that have not been occupied by the fluid phase. For example, orange may be used to represent locations that are occupied by oil.

The visualization can therefore be a visualization of the data or can represent the simulation results, for example, the particular location in the data may represent a voxel in a simulation space. In some implementations, the process 400 may further generate a second visualization of a fluid phase for a subsequent time where a location in the second visualization corresponds to the particular location. The location in the second visualization is colored with a color that represents the amount of elapsed time from then the fluid phase occupies the particular location at the first time until the subsequent time.

In some implementations, locations in the visualization associated with decreased amounts of elapsed time, relative to other amounts of elapsed time of other locations in the visualization, represent a displacement front. In some implementations, the decreased amounts of elapsed time are minimum amounts of elapsed time.

The fluid phase can be a water fluid phase, and the locations in the visualizations that are associated with the decreased amounts of elapsed time represent locations in a pore space at which water has been more recently introduced, relative to other locations in the pore space at which water has been introduced. The location can be a location within or around a porous medium, such as a rock.

In some implementations, the process or the data processing system can adjust (or cause adjustment, e.g., by sending instruction to an external device or entity to adjust) at least one of the fluid phases based on the visualization. The process 400 or the data processing apparatus can also include adjusting (or causing adjustment), based on the visualization, at least one of the two or more fluid phases by adjusting a rate at which fluid of the fluid phase is introduced to a pore space (or physical media, such as a rock sample) or by adjusting a location in the pore space (or physical media) at which the fluid of the fluid phase is introduced into the pore space.

The data processing system (or a client device) can render the visualization. In some implementations, data processing system (or a client device) can render a visualization of the displacement front. In some implementations, the process 400 can be used by the data processing system to generate a video that represents a set of visualizations using a variety of different time intervals.

Figure 5:
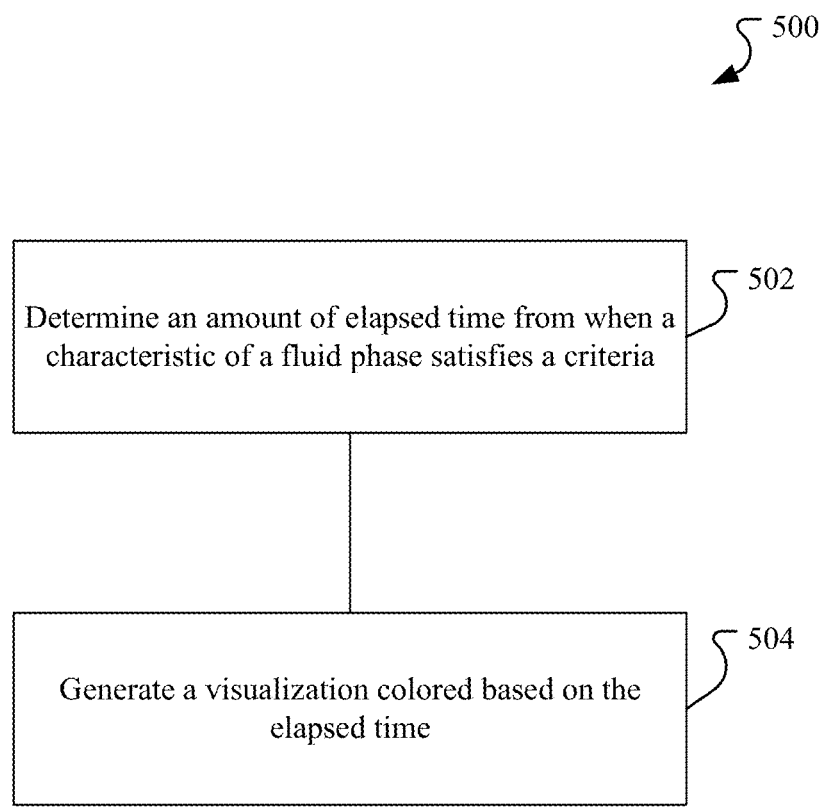

FIG. 5 is a flowchart of another exemplary process 500 for visualizing the flow of two or more fluid phases. The process 500 may be performed by a data processing system that is configured to process instructions stored on a non-transitory computer readable medium, e.g., such as a hardware storage device. The process 500 determines 502 an amount of elapsed time from when one or more characteristics of the fluid phase at a particular location satisfy one or more specified criteria at a first time until a second time. For example, the process 500 can determine an amount of elapsed time from when the velocity of a fluid phase crossed a threshold.

The process 500 generates 504 data for a visualization of the fluid phase, with a location in the visualization corresponding to the particular location, and with the location in the visualization being colored with a color from a set of colors representing the amount of elapsed time. In some implementations, a color may be used to represent locations do not satisfy the criteria (for example, orange).

Figure 6:
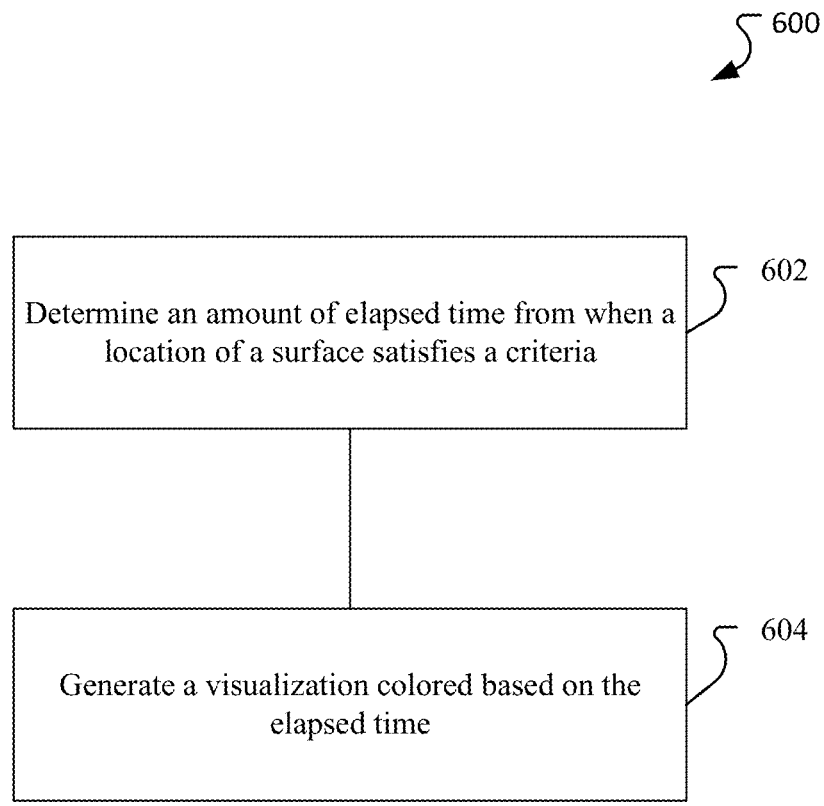

FIG. 6 is a flowchart of another exemplary process 600 for visualizing characteristics of a surface. The process 600 may be performed by a data processing system that is configured to process instructions stored on a non-transitory computer readable medium.

The process 600 determines 602 an amount of elapsed time from when a location of a surface (such as the surface of a rock or other porous medium) satisfies one or more specified criteria at a first time until a second time. For example, the process 600 can determine an amount of elapsed time from when a fluid phase came in contact with the surface at the particular location. In some examples, the surface is a surface of a porous media.

The process 600 generates 604 data for a visualization of the surface, with a location in the visualization corresponding to the particular location being colored with a color from a set of colors representing the amount of elapsed time.

Embodiments of the subject matter and the operations described in this specification can be implemented in digital electronic circuitry, or in computer software, firmware, or hardware, including the structures disclosed in this specification and their structural equivalents, or in combinations of one or more of them. Embodiments of the subject matter described in this specification can be implemented as one or more computer programs (also referred to as a data processing program) (i.e., one or more modules of computer program instructions, encoded on computer storage medium for execution by, or to control the operation of, data processing apparatus). A computer storage medium can be, or be included in, a computer-readable storage device, a computer-readable storage substrate, a random or serial access memory array or device, or a combination of one or more of them. The computer storage medium can also be, or be included in, one or more separate physical components or media (e.g., multiple CDs, disks, or other storage devices). The subject matter may be implemented on computer program instructions stored on a non-transitory computer storage medium.

The operations described in this specification can be implemented as operations performed by a data processing apparatus on data stored on one or more computer-readable storage devices or received from other sources.

The term "data processing apparatus" encompasses all kinds of apparatus, devices, and machines for processing data, including by way of example: a programmable processor, a computer, a system on a chip, or multiple ones, or combinations, of the foregoing. The apparatus can include special purpose logic circuitry (e.g., an FPGA (field programmable gate array) or an ASIC (application specific integrated circuit)). The apparatus can also include, in addition to hardware, code that creates an execution environment for the computer program in question (e.g., code that constitutes processor firmware, a protocol stack, a database management system, an operating system, a cross-platform runtime environment, a virtual machine, or a combination of one or more of them). The apparatus and execution environment can realize various different computing model infrastructures, such as web services, distributed computing and grid computing infrastructures.

A computer program (also known as a program, software, software application, script, or code) can be written in any form of programming language, including compiled or interpreted languages, declarative or procedural languages, and it can be deployed in any form, including as a stand-alone program or as a module, component, subroutine, object, or other unit suitable for use in a computing environment. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform actions by operating on input data and generating output. The processes and logic flows can also be performed by, and apparatus can also be implemented as, special purpose logic circuitry (e.g., an FPGA (field programmable gate array) or an ASIC (application specific integrated circuit)).

Processors suitable for the execution of a computer program include, by way of example, both general and special purpose microprocessors, and any one or more processors of any kind of digital computer. Generally, a processor will receive instructions and data from a read only memory or a random access memory or both. The essential elements of a computer are a processor for performing actions in accordance with instructions and one or more memory devices for storing instructions and data. Generally, a computer will also include, or be operatively coupled to receive data from or transfer data to, or both, one or more mass storage devices for storing data (e.g., magnetic, magneto optical disks, or optical disks), however, a computer need not have such devices. Moreover, a computer can be embedded in another device (e.g., a mobile telephone, a personal digital assistant (PDA), a mobile audio or video player, a game console, a Global Positioning System (GPS) receiver, or a portable storage device (e.g., a universal serial bus (USB) flash drive)). Devices suitable for storing computer program instructions and data include all forms of non-volatile memory, media and memory devices, including by way of example, semiconductor memory devices (e.g., EPROM, EEPROM, and flash memory devices), magnetic disks (e.g., internal hard disks or removable disks), magneto optical disks, and CD ROM and DVD-ROM disks. The processor and the memory can be supplemented by, or incorporated in, special purpose logic circuitry.

To provide for interaction with a user, embodiments of the subject matter described in this specification can be implemented on a computer having a display device (e.g., a CRT (cathode ray tube) or LCD (liquid crystal display) monitor) for displaying information to the user and a keyboard and a pointing device (e.g., a mouse or a trackball) by which the user can provide input to the computer. Other kinds of devices can be used to provide for interaction with a user as well; for example, feedback provided to the user can be any form of sensory feedback (e.g., visual feedback, auditory feedback, or tactile feedback) and input from the user can be received in any form, including acoustic, speech, or tactile input. In addition, a computer can interact with a user by sending documents to and receiving documents from a device that is used by the user (for example, by sending web pages to a web browser on a user's user device in response to requests received from the web browser).

Embodiments of the subject matter described in this specification can be implemented in a computing system that includes a back end component (e.g., as a data server), or that includes a middleware component (e.g., an application server), or that includes a front end component (e.g., a user computer having a graphical user interface or a Web browser through which a user can interact with an implementation of the subject matter described in this specification), or any combination of one or more such back end, middleware, or front end components. The components of the system can be interconnected by any form or medium of digital data communication (e.g., a communication network). Examples of communication networks include a local area network ("LAN") and a wide area network ("WAN"), an inter-network (e.g., the Internet), and peer-to-peer networks (e.g., ad hoc peer-to-peer networks).

The computing system can include users and servers. A user and server are generally remote from each other and typically interact through a communication network. The relationship of user and server arises by virtue of computer programs running on the respective computers and having a user-server relationship to each other. In some embodiments, a server transmits data (e.g., an HTML page) to a user device (e.g., for purposes of displaying data to and receiving user input from a user interacting with the user device). Data generated at the user device (e.g., a result of the user interaction) can be received from the user device at the server.

While this specification contains many specific implementation details, these should not be construed as limitations on the scope of any inventions or of what may be claimed, but rather as descriptions of features specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the embodiments described above should not be understood as requiring such separation in all embodiments, and it should be understood that the described program components and systems can generally be integrated together in a single software product or packaged into multiple software products.

Thus, particular embodiments of the subject matter have been described. Other embodiments are within the scope of the following claims. For example, any of the above techniques that are described with reference to a pore space can also be performed with reference to or with regard to a physical media, such as a rock sample. In some cases, the actions recited in the claims can be performed in a different order and still achieve desirable results. In addition, the processes depicted in the accompanying figures do not necessarily require the particular order shown, or sequential order, to achieve desirable results. In certain implementations, multitasking and parallel processing may be advantageous.

What is claimed is:

1. A method performed by a data processing system for visualizing the behavior of flow of two or more fluid phases to provide detail about a displacement process, wherein a fluid phase behavior is represented in a visualization, the method comprising:
   determining an occupation time, which is the amount of elapsed time from when a fluid phase first occupies a particular location until a second time; and
   rendering on a display of a display device a visualization, with a location in the visualization corresponding to the particular location, and with rendered data for that location in the visualization indicating the occupation time,
   wherein locations in the rendered visualization associated with smaller amounts of occupation time, relative to other amounts of occupation time of other locations in the visualization, represent a displacement front;
   wherein the visualization is included in a video or a set of visualizations representing a progression of the displacement front for a plurality of times.

2. The method of claim 1, wherein the visualization of the fluid phase includes assigning a color based on the occupation time.

3. The method of claim 1, further comprising:
   at a third time subsequent to the second time, updating the occupation time to be the difference between the third time and the first, and
   updating the visualization based on the updated occupation time.

4. The method of claim 1, wherein the fluid phase is a displacing phase, wherein locations with decreased amounts of occupation time, relative to other amounts of occupation time of other locations, represent the displacement front, and wherein the method further comprises:
   generating data for rendering a visualization of the displacement front.

5. The method of claim 1, wherein a fluid phase is a water based or gas based fluid phase.

6. The method of claim 1, wherein the second time comprises a current time.

7. The method of claim 1, wherein the location is a location within or around a porous medium.

8. The method of claim 7, wherein the porous medium is a rock.

9. The method of claim 1, wherein one of the two or more fluid phases represents an oil based fluid phase.

10. The method of claim 1, wherein the location is specified in a data set or in an image.

11. The method of claim 1, further comprising:
    simulating, in a simulation space, flow of two or more fluid phases in a physical media;
    wherein the visualization is a visualization of simulation results.

12. The method of claim 1, wherein the locations in the visualization are represented by a plurality of voxels, wherein each voxel in the visualization includes a color, opacity, shading, texture, and/or other visual indicator representing the occupation time of the location represented by the voxel.

13. The method of claim 1, further comprising rendering the visualization.

14. The method of claim 13, wherein the visualization is included in a video or in a set of visualizations.

15. The method of claim 1, wherein the location in the visualization represents a surface location.

16. A data processing system comprising:
    one or more processor devices;
    memory coupled to the one or more processor devices;
    storage media storing executable computer instructions for visualizing the behavior of flow of two or more fluid phases to provide detail about a displacement process, the instructions to configure the one or more processors to:
       determine an occupation time, which is the amount of elapsed time from when a fluid phase first occupies a particular location until a second time; and render on a display of a display device a visualization, with a location in the visualization corresponding to the particular location, and with rendered data for that location in the visualization indicating the occupation time, wherein locations in the rendered visualization associated with smaller amounts of occupation time, relative to other amounts of occupation time of other locations in the visualization, represent a displacement front;

wherein the visualization is included in a video or a set of visualizations representing a progression of the displacement front for a plurality of times.

17. The data processing system of claim 16, wherein the instructions further comprise:

at a third time subsequent to the second time, update the occupation time to be the difference between the third time and the first, and update the visualization based on the updated occupation time.

18. A computer program product tangibly stored on a computer readable non-transitory storage device that stores executable computer instructions to visualizing the behavior of flow of two or more fluid phases to provide detail about a displacement process, the instructions for causing a computing system to:

determine an occupation time, which is the amount of elapsed time from when a fluid phase first occupies a particular location until a second time; and render on a display of a display device a visualization, with a location in the visualization corresponding to the particular location, and with rendered data for that location in the visualization indicating the occupation time, wherein locations in the rendered visualization associated with smaller amounts of occupation time, relative to other amounts of occupation time of other locations in the visualization, represent a displacement front;

wherein the visualization is included in a video or a set of visualizations representing a progression of the displacement front for a plurality of times.

19. The computer program product of claim 18, wherein the instructions further comprise:

at a third time subsequent to the second time, update the occupation time to be the difference between the third time and the first, and update the visualization based on the updated occupation time.

* * * * *